(12) United States Patent
Miff et al.

(10) Patent No.: US 12,087,449 B2
(45) Date of Patent: Sep. 10, 2024

(54) PERSONAL PANDEMIC PROXIMITY INDEX SYSTEM AND METHOD

(71) Applicant: Parkland Center for Clinical Innovation, Dallas, TX (US)

(72) Inventors: Steve Miff, Dallas, TX (US); Akshay Arora, Irving, TX (US); Mansi Kukreja, Dallas, TX (US); Albert Karam, Garland, TX (US); Manjula Julka, Plano, TX (US); George Oliver, Southlake, TX (US)

( * ) Notice: Subject to any disclaimer, the term of this patent is extended or adjusted under 35 U.S.C. 154(b) by 508 days.

(21) Appl. No.: 17/327,259

(22) Filed: May 21, 2021

(65) Prior Publication Data

US 2021/0366621 A1 Nov. 25, 2021

Related U.S. Application Data

(60) Provisional application No. 63/028,534, filed on May 21, 2020.

(51) Int. Cl.
| | | |
|---|---|---|
| *G16H 50/80* | (2018.01) | |
| *G06F 40/20* | (2020.01) | |
| *G06N 20/00* | (2019.01) | |
| *G16H 50/30* | (2018.01) | |

(52) U.S. Cl.
CPC .............. *G16H 50/80* (2018.01); *G06F 40/20* (2020.01); *G06N 20/00* (2019.01); *G16H 50/30* (2018.01)

(58) Field of Classification Search
CPC ........ G16H 50/80; G16H 50/30; G06F 40/20; G06N 20/00; G06N 20/10

USPC .................................................. 700/90–212
See application file for complete search history.

(56) References Cited

U.S. PATENT DOCUMENTS

| 11,056,242 B1 * | 7/2021 | Jain ..................... G16H 10/60 |
| 11,456,080 B1 * | 9/2022 | Jain ..................... A61B 5/4815 |
| 11,504,011 B1 * | 11/2022 | Jain ......................... G06N 5/04 |
| 2010/0097209 A1 * | 4/2010 | Wong .................... G01S 5/0284 |
| | | 340/539.13 |
| 2019/0172564 A1 * | 6/2019 | Chandra ................ G06N 20/00 |
| 2020/0294680 A1 * | 9/2020 | Gupta .................... G16H 40/20 |

OTHER PUBLICATIONS

Dong, Wen, et al. "PocketCare: Tracking the flu with mobile phones using partial observations of proximity and symptoms." Proceedings of the ACM on Interactive, Mobile, Wearable and Ubiquitous Technologies 3.2 (2019): pp. 1-23. (Year: 2019).*

(Continued)

*Primary Examiner* — Satish Rampuria
(74) *Attorney, Agent, or Firm* — Fulton Jeang PLLC; Wei Wei Jeang

(57) ABSTRACT

The personal pandemic proximity index system and method include a data ingestion pipeline configured to receive location data associated with disease-positive cases, a data processing module configured to clean and process the received data, a personal pandemic proximity module configured to determine a numerical personal pandemic proximity index value associated with an individual having an interaction at an address relative to the location data, and a graphical user interface configured to present, to a patient care team, the numerical personal pandemic proximity index value, which may include a modified workflow to limit the spread of disease.

15 Claims, 7 Drawing Sheets

(56) References Cited

OTHER PUBLICATIONS

Wang, Jin-Feng, et al. "Data-driven exploration of 'spatial pattern-time process-driving forces' associations of SARS epidemic in Beijing, China." Journal of Public Health 30.3 (2008): pp. 234-244. (Year: 2008).*

Glass, Gregory E., et al. "Using remotely sensed data to identify areas at risk for hantavirus pulmonary syndrome." Emerging infectious diseases 6.3 (2000): pp. 238-247. (Year: 2000).*

* cited by examiner

PERSONAL PANDEMIC PROXIMITY INDEX SYSTEM AND METHOD

RELATED APPLICATION

This patent application claims the benefit of U.S. Provisional Patent Application No. 63/028,534 filed on May 21, 2020, all of which is incorporated herein by reference.

FIELD

The present disclosure relates to a system and method that generates a real-time personal pandemic/infectious disease proximity index (PPPI).

DETAILED DESCRIPTION

Management of pandemic spread such as COVID-19 has tested the healthcare, political, and social fabric of communities around the world. For all, the term "flatten the curve" has come to represent how specific measures, such as social distancing, mask wearing, lock-down, and quarantine can slow the spread of the virus, which in turn can help to mitigate the tidal surge that would overwhelm the capacity of the healthcare system. For any region, there is a critical window of opportunity to leverage advanced analytics, geospatial modeling (hot-spotting), and integrated patient-management tools to better equip civic leaders and care delivery teams with real-time information to mitigate the surge and save more lives. Further, frontline clinical staff need real-time information about patient proximity to infected individuals to use in addition to clinical manifestation to assess risk of exposure to the virus for effective testing, triage, prioritization, and follow-up (through texting and other means). A real-time, patient-specific personal proximity index is needed at the point-of-care to effectively empower frontline staff to better manage asymptomatic patients who may nevertheless unwittingly pass the virus to others.

Figure 1:
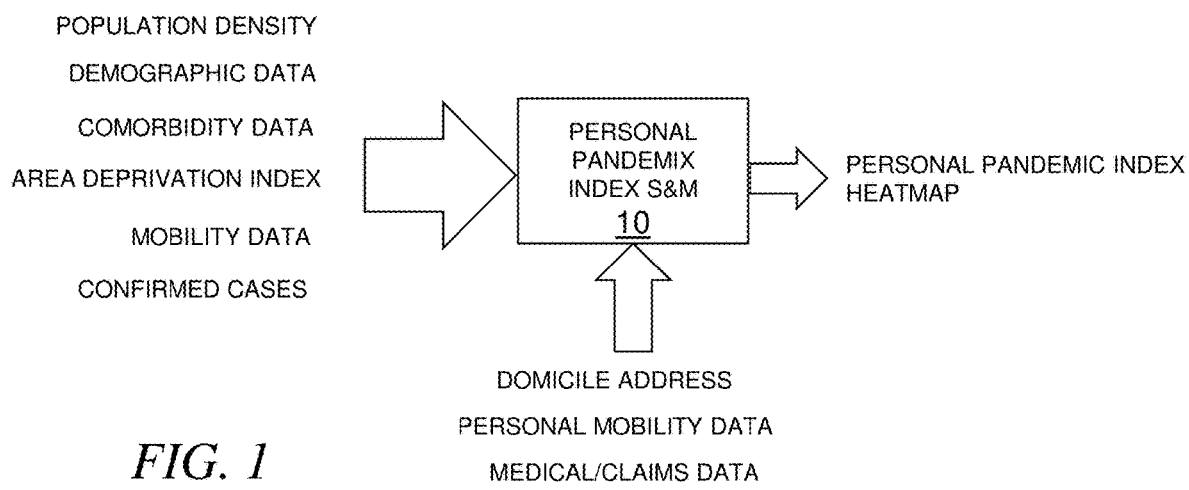
FIG. 1 is a simplified block diagram of the system and method for generating real-time personal pandemic proximity index according to the teachings of the present disclosure.
Figure 2:
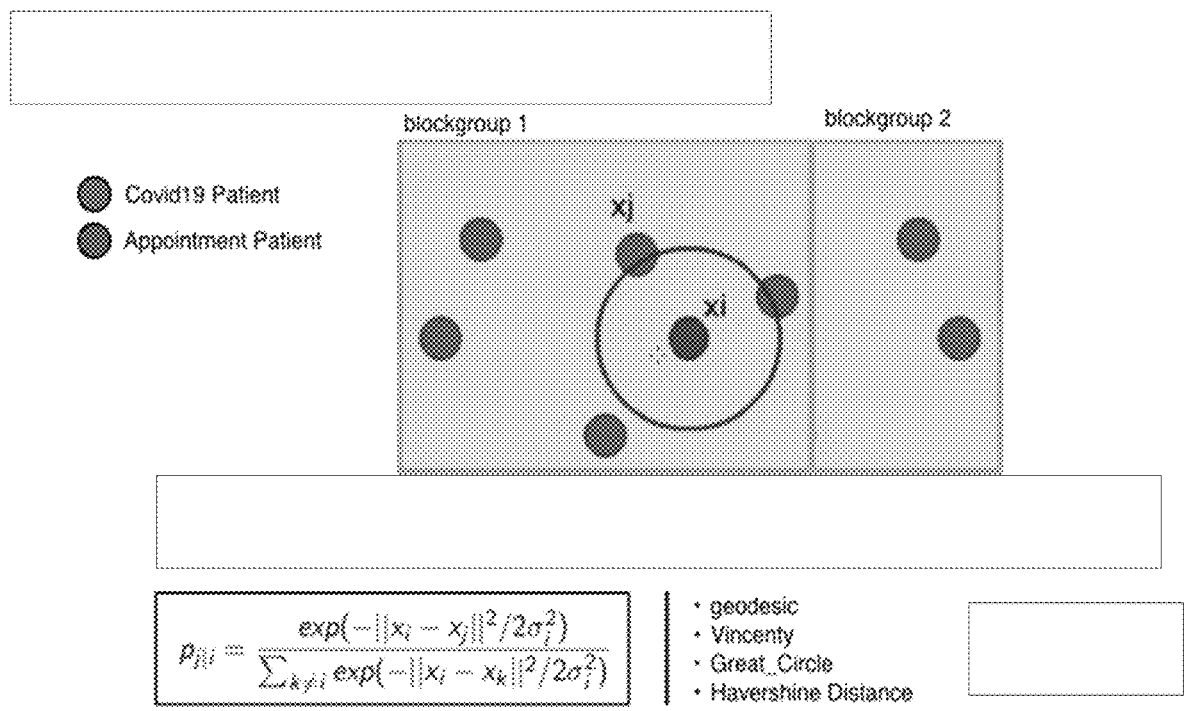
FIG. 2 is a simplified diagram illustrating estimating an individual's geospatial-driven exposure risk propensity using a Gaussian formulation centered where active disease cases are identified according to the teachings of the present disclosure.

As shown in FIG. 1, the system and method 10 determine a personal pandemic proximity index (PPPI) for each person based on a variety of factors, including domicile address, population density associated with the domicile address, personal mobility information, and identified disease-positive persons, addresses, and hotspots. This mobility data includes transactional data such as credit card purchases, mobile aps geolocation from sources such as Facebook®, Google®, Apple®, etc. and the distance traveled/mode of transportation of an individual and groups over a period of time. The system and method perform analyses uses data of confirmed infection cases, population density, and areas of individuals at high risk for disease complications. Census-based data can be analyzed with the longitudinal hospital claims data for a more complete view. For example, it is known that individuals with certain medical conditions and those who are on certain immune suppressant medications are more susceptible to COVID-19 infections. As shown in FIG. 2, this information can be extracted from claims data, and aggregated to a block group level to identify block groups that are more vulnerable to COVID-19 spread. A census block group is a geographical unit used by the United States Census Bureau which is between the census tract and the census block. It is the smallest geographical unit for which the bureau publishes sample data, i.e., data which is only collected from a fraction of all households. Typically, block groups have a population of 600 to 3,000 people. Using geospatial modeling, emerging hotspots across a certain city, county, state, or other regions can be identified. Geospatial-driven exposure risk propensity is estimated using a Gaussian formulation centered where active COVID-19 cases are identified. This is different from traditional SIR, SEIR and SEIRS models that have been commonly used to simulate epidemic progression through susceptible, exposed, infectious, recovered, and susceptible stages. Individuals within threshold geographical distances (that can be set according to scientific data) can be considered to be at-risk. The primary cohorts of individuals to apply the risk index are the general population, hospital employees and their beneficiaries, patients in or arriving at prisons, nursing homes, and other high risk populations based on age, comorbidities and social economic status.

Figure 3:
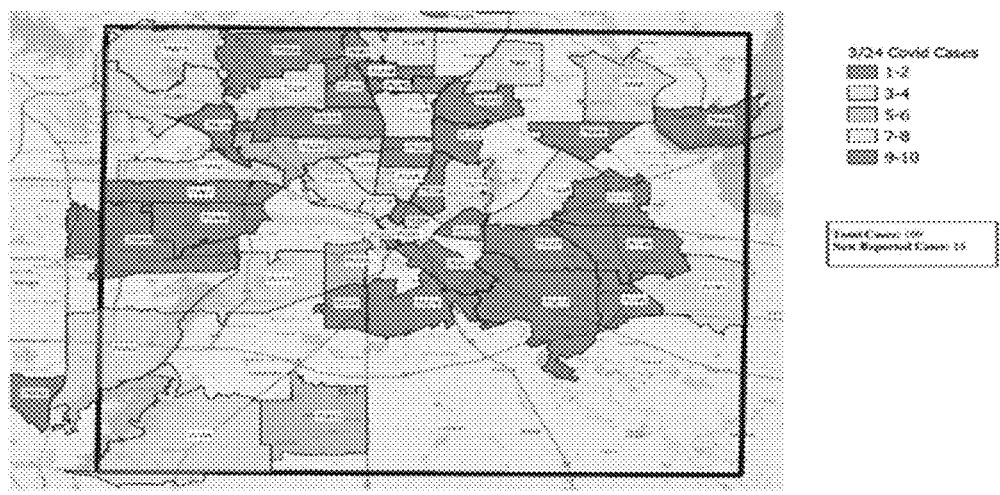
FIG. 3 is an example map plot GUI of data at the zip code or block group level according to the teachings of the present disclosure.
Figure 4:
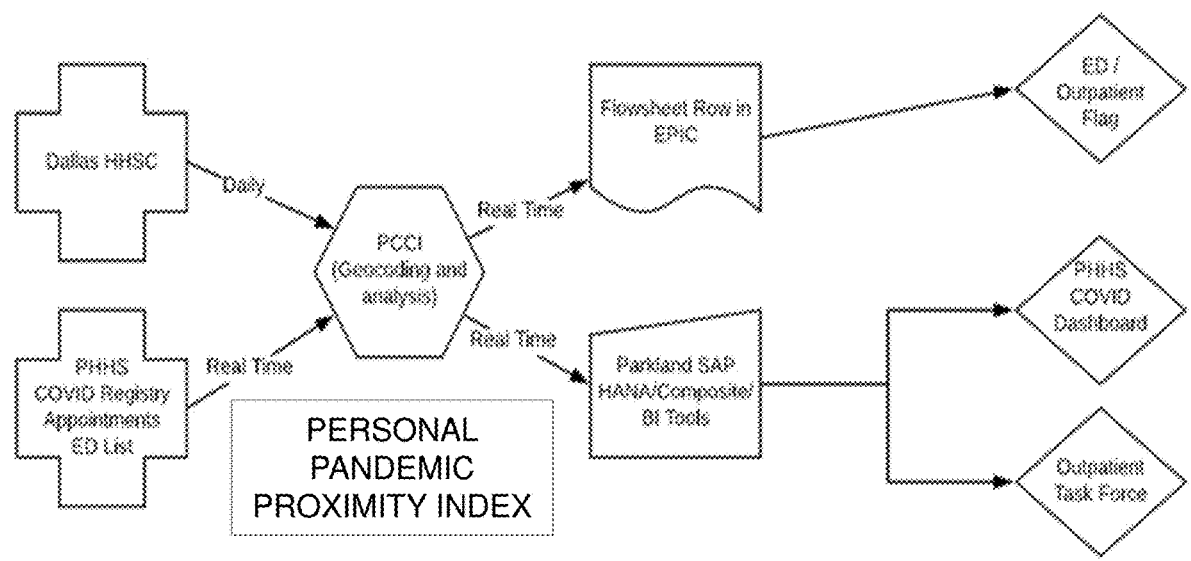
FIG. 4 is a simplified flowchart according to the teachings of the present disclosure.

As shown in FIG. 3, a real-time graphical user interface (GUI) displays a map of the geographical region in question, such as a city, county, state, region, and country. The map shows geospatially how the confirmed case hotspots are evolving. The map has one or more overlay layers that show locations of hospitals, testing centers, outpatient clinics, vaccination sites, etc. to assess needs for additional sites. Correlations are drawn between community density (population per square feet) or demographics with the prevalence of confirmed cases to recommend civic hygiene-related messaging/public worker visits in targeted areas (e.g., low-income apartments). Individuals' mobility data (from mobile devices) can be incorporated to show spheres of activity of confirmed cases so that advisory messages may be transmitted to affected individuals as well as give data to frontline professionals such as police/fire/local hospitals to enhance the radiuses of their patients-at-risk triage and treatment procedures. If there are emerging hotspots of current cases close to the most vulnerable neighborhoods, this will be the signal for city leaders and hospital administrators to prioritize additional testing, hospital capacity, or other resources for those neighborhoods. It may also be used to deploy additional protective or quarantine methods with more precision rather than implementing a metroplex-wide lockdown. This ensures that decision-makers can use appropriate and necessary strategies to contain and mitigate outbreaks and hotspots, as well as provide this critical information to frontline healthcare providers. The GUI intentionally removes or excludes patient personal identifiable information such as names, specific addresses, driver's license numbers, social security numbers, etc. Patient-level information will only be used within the workflows of a specific healthcare institution or system, for example if a particular individual checks in at an emergency department of a healthcare location. For any use external to the healthcare institution or system, all data will be aggregated up to a predetermined grouping, such as the block group level. Access to the GUI can also be limited to specific healthcare professionals, city and county leaders, etc. with the proper access credentials.

Frontline clinical staff need real-time information about patient proximity to infected individuals (patients and staff) to use in addition to clinical manifestation to assess risk of disease exposure for effective isolation, testing, triage, prioritization, treatment, and follow-up. A real-time, patient-specific proximity index is needed at the point-of-care to effectively empower frontline staff. Having insights about individuals who are at greater risk of contracting a contagious disease is important but integrating insights into clinical workflows is absolutely vital for changing the trajectory of a pandemic. As such, healthcare workflows are revised to integrate the PPPI for active patient management.

The present system and method may incorporate machine learning and artificial intelligence in data analysis to derive the PPPI. The PPPI data is presented graphically with sufficient granularity to aid in comprehension and incorporated in clinical workflows to make them actionable. The GUI generates highly specific, block group-level indicators from a variety of publicly available data sources and present the data analysis via a highly interactive and user-friendly geospatial GUI that are adaptable for a variety of computing platforms. The GUI provides actionable insights that enable community and civic leaders to more optimally deploy and manage physical distancing and quarantine tools. The data sources used include both publicly available and proprietary/licensed data such as the census and pandemic tracking governmental sites, Facebook® data, Google® data, Apple® data, SafeGraph® data, Hospital data, jail health data, employee benefits and plan data, homeless shelter and food bank data, and nursing home data.

The PPPI identifies high-risk patients who are scheduled for outpatient services within, for example, the next 48 hours. The PPPI also identifies, in real-time, patients at high risk for COVID-19 when they seek care at the Emergency Department (ED). This data-driven approach provides frontline clinical teams to better anticipate patients at high risk for COVID-19 so that precautions can be taken to reduce risk of disease spread.

Through an automated pipeline using, e.g., Apache NiFi, raw data is received by the Azure Blob Storage, using File Transfer Protocol (FTP), Simple Object Database Access (SODA)/Application Program Interface (API), client URL (cURL), and other methods. Data is automatically pulled from the sources on a regular basis to ensure that the current data is the most up to date. The Blob Storage cleans the data for quality and accuracy according to predefined scripts. Cleaned data are then moved within the Azure environment to the PostgreSQL database management system and stored in a tabular format.

Figure 5:
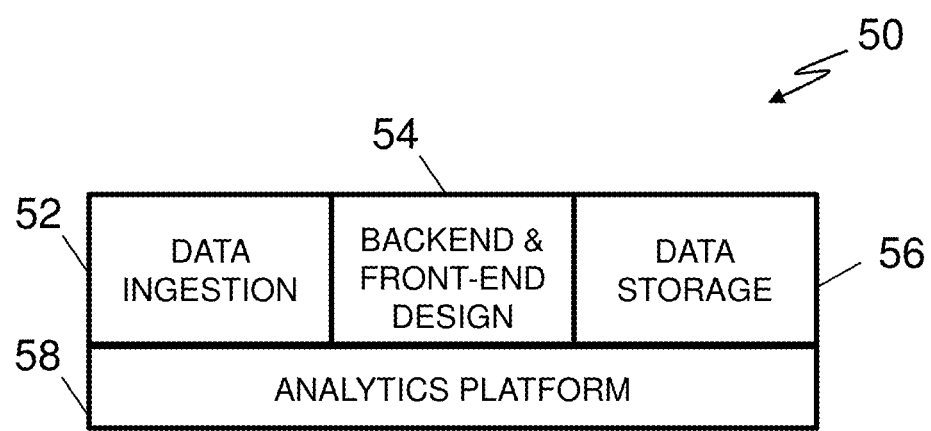
FIG. 5 is a simplified block diagram of the hardware components of an embodiment of the personal pandemic proximity index system and method according to the teachings of the present disclosure.

As shown in FIG. 5, the architecture 50 includes a data ingestion layer 52, a backend and front-end design layer 54, and a storage layer 56 that sits on top of an analytics platform 58 that may be hosted in the Azure infrastructure.

The PPPI GUI may use the Power BI GUI tool to pull data from the PostgreSQL database management system. Power BI is a Microsoft product and easily integrates with the Azure platform. Four GUIs were set up based on use cases identified by external and internal stakeholders, including education, community needs, health, and economy and public safety. Additionally, a master GUI was created to provide users the opportunity to look at how indicators interact across categories. The GUI also uses a mapping application, MapBox, that integrates well into the Power BI platform. The Power BI GUI can be embedded into a PPPI web portal, where users can use it to gain actionable insights into the Dallas community (or other geographical/geopolitical regions).

Figure 6:
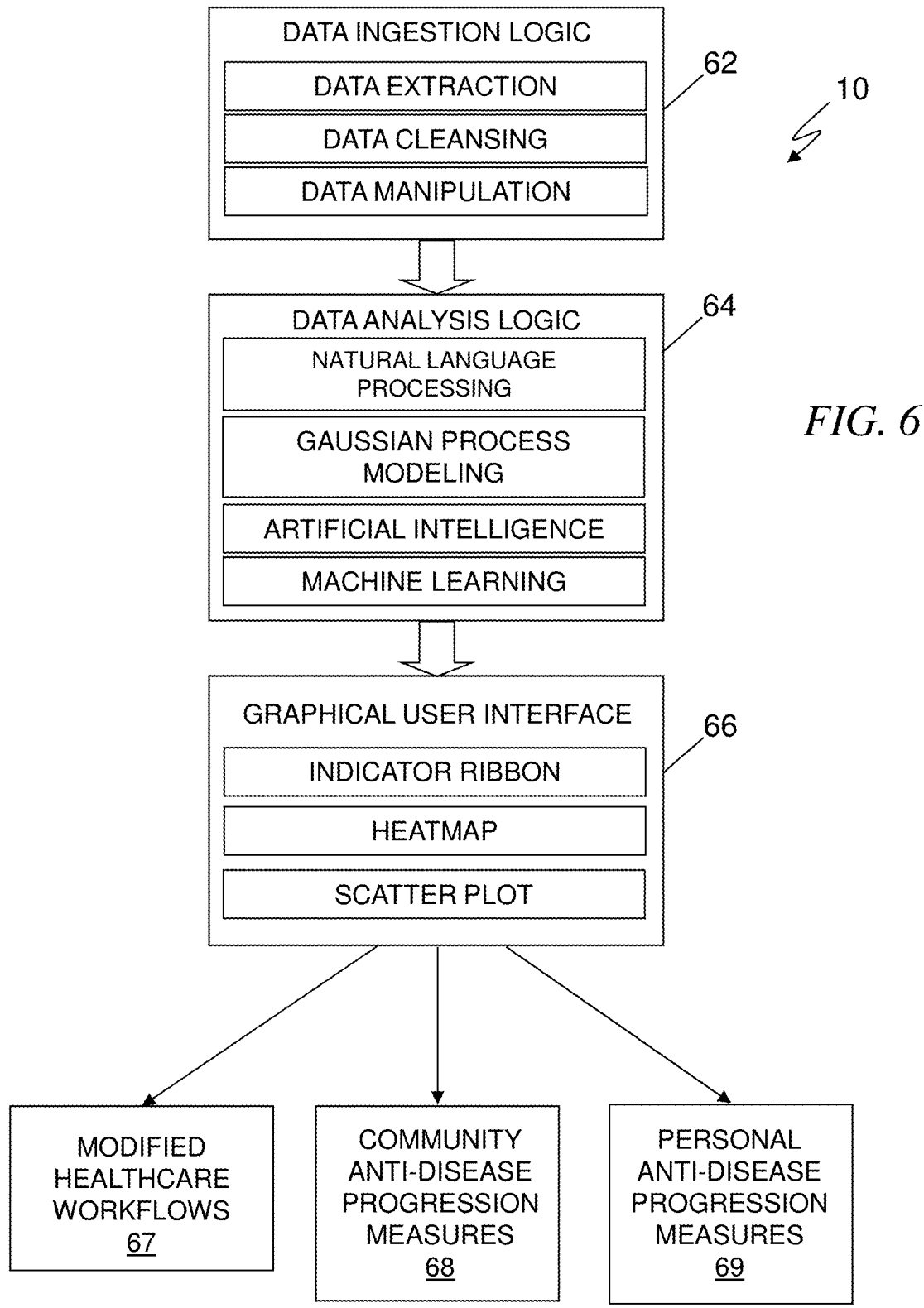
FIG. 6 is a simplified flow diagram of an embodiment of the personal pandemic proximity index system and method according to the teachings of the present disclosure.

As shown in FIG. 6, a data ingestion logic 62, including logic extracts relevant data, cleansing the data, and manipulate the data, receives and processes the data so that they may be analyzed by a data analysis logic module. A data analysis logic module 64 includes artificial intelligence (AI), machine learning (ML), and natural language processing (NLP) to analyze the ingested data. NLP is used, for example, to process raw data pulled from Dallas County Health and Human Services (DCHHS) and COVID-19 disease registry. Specifically, NLP is used to match patients to the various data sources for identifying both those tested and confirmed positive for the disease. The data cleansing process "cleans" or pre-processes the data, putting structured data in a standardized format and preparing unstructured text for NLP. This logic module may also convert the data into desired formats (e.g., text date field converted to numeric for calculation purposes). A number of complex natural language processing functions including text preprocessing, lexical analysis, syntactic parsing, semantic analysis, handling multi-word expression, word sense disambiguation, and other functions may be performed. A Gaussian process modeling logic module analyzes the data to determine geospatial-driven exposure risk propensity using a Gaussian formulation centered where active COVID-19 cases are identified. The GUI 16 presents the data in a number of ways, including an indicator ribbon, a scatter plot, and a heatmap. The PPPI data generated by the system and method 10 may be used to automatically modify healthcare workflows 67, design and institute anti-disease progression measures 68, and inform individuals so that they may formulate their own personal anti-disease progression measures 69. For example, based on a patient's PPPI value, certain protective devices should be deployed when care team members are interacting with this patient. The system 10 may automatically provide a modified workflow based on the PPPI value for a patient.

Figure 7:
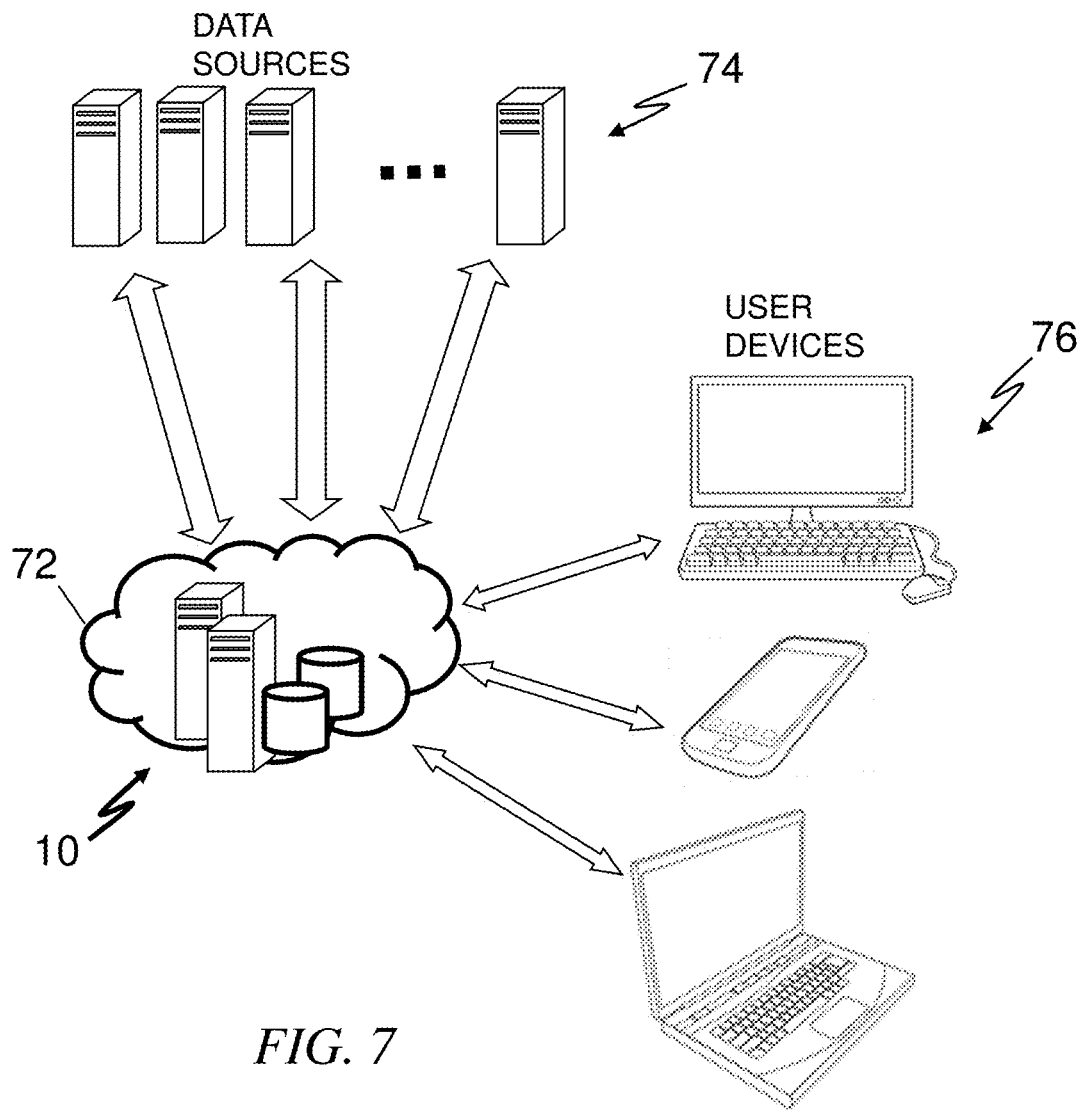
FIG. 7 is a simplified block diagram of the exemplary operating environment of the personal pandemic proximity index system and method.

Referring to FIG. 7, The system and method 10 are hosted, for example, on the Microsoft Azure Cloud 72. By hosting everything on a single platform in an exemplary embodiment, the system 10 is a streamlined process for ingesting data from disparate data sources 74, and for cleaning, extracting, and analyzing the data. The data presentation is performed on user devices 76 that may include mobile phones, laptops, notepad computers, desktop computers, and other display devices.

The features of the present invention which are believed to be novel are set forth below with particularity in the appended claims. However, modifications, variations, and changes to the exemplary embodiments described above will be apparent to those skilled in the art, and the system and method described herein thus encompasses such modifications, variations, and changes and are not limited to the specific embodiments described herein.

What is claimed is:

1. A personal pandemic proximity index system comprising:
   a data ingestion pipeline receives location data associated with disease-positive cases;
   a data processing module cleans and processes the received data;
   a personal pandemic proximity module determines a numerical personal pandemic proximity index value associated with an individual having an interaction at an address relative to the location data;
   a graphical user interface presents, to a patient care team, the numerical personal pandemic proximity index value; and
   the graphical user interface further presents, to a pandemic management team, a map displaying locations of disease-positive cases and showing the geospatial relationship of individual's address to the disease-positive cases;
   wherein the data ingestion pipeline further receives mobility data associated with disease-positive cases, and the personal pandemic proximity module further determines the numerical personal pandemic proximity index value based at least in part on the mobility data;
   wherein the data processing module processes the received data using at least one of artificial intelligence and machine learning techniques.

2. The system of claim 1, wherein the data processing module processes the received data using natural language processing techniques.

3. The system of claim 1, wherein the data processing module processes the received data using Gaussian process modeling techniques.

4. The system of claim 1, wherein the graphical user interface to displays the heatmap showing data at a block-group level.

5. The system of claim 1, wherein the graphical user interface displays a recommended modified workflow for the patient care team.

6. A personal pandemic proximity index method comprising: receiving location data associated with disease-positive cases; extracting and processing the received data;
   determining a numerical personal pandemic proximity index value associated with an individual having an address relative to the location data;
   presenting, to a patient care team, the numerical personal pandemic proximity index value associated with the individual; and
   presenting a heatmap displaying locations of disease-positive cases and showing the geospatial relationship of the individual's address to the disease-positive cases;
   wherein receiving the location data comprises receiving mobility data associated with disease-positive cases, and determining the numerical personal pandemic proximity index value based at least in part on the mobility data;
   wherein determining the numerical personal pandemic proximity index value comprises processing the received data using at least one of artificial intelligence and machine learning techniques.

7. The method of claim 6, wherein determining the numerical personal pandemic proximity index value comprises processing the received data using natural language processing techniques.

8. The method of claim 6, wherein determining the numerical personal pandemic proximity index value comprises processing the received data using Gaussian process modeling techniques.

9. The method of claim 6, wherein presenting the heatmap comprises displaying the heatmap showing data at a block-group level.

10. The method of claim 6, further comprising presenting a recommended modified workflow for the patient care team based at least in part on the numerical personal pandemic proximity index value associated with the individual.

11. A database management system having encoded thereon a method for determining a personal pandemic proximity index, the method comprising:
    receiving location data associated with disease-positive cases;
    extracting and processing the received data;
    determining a numerical personal pandemic proximity index value associated with an individual having an address relative to the location data;
    presenting, to a patient care team, the numerical personal pandemic proximity index value associated with the individual; and
    presenting a heatmap displaying locations of disease-positive cases and showing the geospatial relationship of the individual's address to the disease-positive cases;
    wherein receiving the location data comprises receiving mobility data associated with disease-positive cases, and determining the numerical personal pandemic proximity index value based at least in part on the mobility data;
    wherein determining the numerical personal pandemic proximity index value comprises processing the received data using at least one of artificial intelligence and machine learning techniques.

12. The database management system of claim 11, wherein determining the numerical personal pandemic proximity index value comprises processing the received data using natural language processing techniques.

13. The database management system of claim 11, wherein determining the numerical personal pandemic proximity index value comprises processing the received data using Gaussian process modeling techniques.

14. The database management system of claim 11, wherein presenting the heatmap comprises displaying the heatmap showing data at a block-group level.

15. The database management system of claim 11, further comprising: presenting a recommended modified workflow for the patient care team based at least in part on the numerical personal pandemic proximity index value associated with the individual.

* * * * *